US011129852B2

(12) United States Patent
Offen et al.

(10) Patent No.: US 11,129,852 B2
(45) Date of Patent: Sep. 28, 2021

(54) MESENCHYMAL CELL-DERIVED EXOSOMES TO TREAT NEUROLOGICAL DISORDERS

(71) Applicant: RAMOT AT TEL-AVIV UNIVERSITY LTD., Tel-Aviv (IL)

(72) Inventors: Daniel Offen, Tel-Aviv (IL); Nisim Perets, Tel-Aviv (IL)

(73) Assignee: RAMOT AT TEL AVIV UNIVERSITY LTD., Tel Aviv (IL)

( * ) Notice: Subject to any disclaimer, the term of this patent is extended or adjusted under 35 U.S.C. 154(b) by 306 days.

(21) Appl. No.: 16/325,445

(22) PCT Filed: Aug. 14, 2017

(86) PCT No.: PCT/IL2017/050899
§ 371 (c)(1),
(2) Date: Feb. 14, 2019

(87) PCT Pub. No.: WO2018/033911
PCT Pub. Date: Feb. 22, 2018

(65) Prior Publication Data
US 2019/0209621 A1 Jul. 11, 2019

Related U.S. Application Data

(60) Provisional application No. 62/374,852, filed on Aug. 14, 2016.

(51) Int. Cl.
*A61K 35/28* (2015.01)
*A61P 25/28* (2006.01)
*A61P 25/18* (2006.01)
*A61K 9/00* (2006.01)
*A61K 9/127* (2006.01)

(52) U.S. Cl.
CPC ............ *A61K 35/28* (2013.01); *A61K 9/0043* (2013.01); *A61K 9/127* (2013.01); *A61P 25/18* (2018.01); *A61P 25/28* (2018.01)

(58) Field of Classification Search
CPC .................................................. A61K 35/28
See application file for complete search history.

(56) References Cited

U.S. PATENT DOCUMENTS

| 3,791,932 | A | 2/1974 | Schuurs |
| 3,839,153 | A | 10/1974 | Schuurs |
| 3,850,578 | A | 11/1974 | McConnell |
| 3,850,752 | A | 11/1974 | Schuurs |
| 3,853,987 | A | 12/1974 | Dreyer |
| 3,867,517 | A | 2/1975 | Ling |
| 3,879,262 | A | 4/1975 | Schuurs |
| 3,901,654 | A | 8/1975 | Gross |
| 3,935,074 | A | 1/1976 | Rubenstein |
| 3,984,533 | A | 10/1976 | Uzgiris |
| 3,996,345 | A | 12/1976 | Ullman |
| 4,034,074 | A | 7/1977 | Miles |
| 4,098,876 | A | 7/1978 | Piasio |
| 4,666,828 | A | 5/1987 | Gusella |
| 4,683,202 | A | 7/1987 | Mullis |
| 4,801,531 | A | 1/1989 | Frossard |
| 4,879,219 | A | 11/1989 | Wands |
| 5,011,771 | A | 4/1991 | Bellet |
| 5,192,659 | A | 3/1993 | Simons |
| 5,272,057 | A | 12/1993 | Smulson |
| 5,281,521 | A | 1/1994 | Trojanowski |
| 5,486,359 | A | 1/1996 | Caplan |
| 9,629,879 | B2 | 4/2017 | Corteling |
| 2011/0014251 | A1 | 1/2011 | Ray |
| 2013/0143314 | A1* | 6/2013 | Shiels ................ G01N 33/5061 435/320.1 |
| 2015/0079046 | A1 | 3/2015 | Sinden |
| 2015/0190430 | A1 | 7/2015 | Lim |

FOREIGN PATENT DOCUMENTS

| EP | 2254586 | B1 | 4/2015 |
| JP | 2011219432 | A | 11/2011 |
| JP | 2012508733 | A | 4/2012 |
| JP | 2016065106 | A | 4/2016 |
| WO | 2012156968 | A2 | 11/2012 |
| WO | 2013150303 | A1 | 10/2013 |
| WO | 2013186735 | A2 | 12/2013 |
| WO | 2016149358 | A1 | 9/2016 |

OTHER PUBLICATIONS

Jarmalavičiūtū u et al. (Exosomes from dental pulp stem cells rescue human dopaminergic neurons from 6-hydroxy-dopamine-induced apoptosis. Cytotherapy, 2015; 17:932-939). (Year: 2015).*
Ruenn Chai Lai et al. ("Chapter 3 Mesenchymal Stem Cell Exosomes" The future MSC-Based Therapy? L.G. Chase and M.C. Vemuri (eds.), Mesenchymal Stem Cell Therapy, Stem Cell Biology and Regenerative Medicine, DOI 10.1007/978-1-62703-200-1_3, ©Springer Science+Business Media New York 2013) (Year: 2013).*
Ashwood et al., (2011) In search of cellular immunophenotypes in the blood of children with autism. PLoS One 6(5): e19299; 9 pages.
Ashwood et al., (2011) Associations of impaired behaviors with elevated plasma chemokines in autism spectrum disorders. J Neuroimmunol 232(1-2): 196-199.
Ashwood et al., (2011) Altered T cell responses in children with autism. Brain Behav Immun 25(5): 840-849.
Blenner et al., (2011) Diagnosis and management of autism in childhood. BMJ 343: d6238; pp. 894-899 and correction.
Bolivar et al., (2007) Assessing autism-like behavior in mice: variations in social interactions among inbred strains. Behav Brain Res 176(1): 21-26.

(Continued)

*Primary Examiner* — Scott Long
(74) *Attorney, Agent, or Firm* — Browdy and Neimark, PLLC

(57) ABSTRACT

A method of treating a neurological disease (such as autism) in a subject is disclosed. The method comprises administering to the subject a therapeutically effective amount of microparticles derived from mesenchymal stem cells.

17 Claims, 14 Drawing Sheets

(56) References Cited

OTHER PUBLICATIONS

Colter et al., (2000) Rapid expansion of recycling stem cells in cultures of plastic-adherent cells from human bone marrow. Proc Natl Acad Sci U S A 97(7): 3213-3218.
Doeppner et al., (2015) Extracellular Vesicles Improve Post-Stroke Neuroregeneration and Prevent Postischemic Immunosuppression. Stem Cells Transl Med 4(10): 1131-1143.
Guariglia and Chadman (2013) Water T-maze: a useful assay for determination of repetitive behaviors in mice. J Neurosci Methods 220(1): 24-29.
Jones et al., (2002) Isolation and characterization of bone marrow multipotential mesenchymal progenitor cells. Arthritis Rheum 46(12): 3349-3360.
Karvat and Kimchi (2014) Acetylcholine elevation relieves cognitive rigidity and social deficiency in a mouse model of autism. Neuropsychopharmacology 39(4): 831-840.
Kawikova and Askenase (2015) Diagnostic and therapeutic potentials of exosomes in CNS diseases. Brain Res 1617: 63-71.
Li et al., (2009) Elevated Immune Response in the Brain of Autistic Patients. J Neuroimmunol 207(1-2): 111-116.
Marlin et al., (2015) Oxytocin enables maternal behaviour by balancing cortical inhibition. Nature 520(7548): 499-504.
McCloy et al., (2014) Partial inhibition of Cdk1 in G 2 phase overrides the SAC and decouples mitotic events. Cell cycle 13(9): 1400-1412.
Meldolesi (2016) Ectosomes and exosomes-two extracellular vesicles that differ only in some details. Biochemistry & Molecular Biology Journal 2(1): 3; 4 pages.
Nickl-Jockschat and Michel (2011) The role of neurotrophic factors in autism. Mol Psychiatry 16(5): 478-490.
Perets et al., (2017) Long term beneficial effect of neurotrophic factors-secreting mesenchymal stem cells transplantation in the BTBR mouse model of autism. Behav Brain Res 331: 254-260.
Sadan et al., (2012) Intrastriatal transplantation of neurotrophic factor-secreting human mesenchymal stem cells improves motor function and extends survival in R6/2 transgenic mouse model for Huntington's disease. PLoS Curr 4: e4f7f6dc013d4e; 11 pages.
Sadan et al., (2012) Mesenchymal stem cells induced to secrete neurotrophic factors attenuate quinolinic acid toxicity: a potential therapy for Huntington's disease. Exp Neurol 234(2): 417-427.
Salem and Thiemermann (2010) Mesenchymal stromal cells: current understanding and clinical status. Stem Cells 28 (3): 585-596.
Segal-Gavish et al., (2016) Mesenchymal Stem Cell Transplantation Promotes Neurogenesis and Ameliorates Autism Related Behaviors in BTBR Mice. Autism Res 9(1): 17-32.
Silverman et al., (2013) Ampakine enhancement of social interaction in the BTBR mouse model of autism. Neuropharmacology 64: 268-282.
Simmons and Torok-Storb (1991) Identification of stromal cell precursors in human bone marrow by a novel monoclonal antibody, STRO-1. Blood 78(1): 55-62.
Stephenson et al., (2011) Histopathologic characterization of the BTBR mouse model of autistic-like behavior reveals selective changes in neurodevelopmental proteins and adult hippocampal neurogenesis. Mol Autism 2(1): 7; 22 pages.
Uccelli et al., (2011) Mesenchymal stem cells for the treatment of multiple sclerosis and other neurological diseases. Lancet Neurol 10(7): 649-656.
Valadi et al., (2007) Exosome-mediated transfer of mRNAs and microRNAs is a novel mechanism of genetic exchange between cells. Nat Cell Biol 9(6): 654-659.
Wegiel et al., (2010) The neuropathology of autism: defects of neurogenesis and neuronal migration, and dysplastic changes. Acta Neuropathol 119(6): 755-770.
Xin et al., (2013) Systemic administration of exosomes released from mesenchymal stromal cells promote functional recovery and neurovascular plasticity after stroke in rats. J Cereb Blood Flow Metab 33(11): 1711-1715.
Yu et al., (2014) Exosomes derived from mesenchymal stem cells. Int J Mol Sci 15(3): 4142-4157.
Zhang et al., (2015) Effect of exosomes derived from multipluripotent mesenchymal stromal cells on functional recovery and neurovascular plasticity in rats after traumatic brain injury. J Neurosurg 122(4): 856-867.
Zhuang et al., (2011) Treatment of Brain Inflammatory Diseases by Delivering Exosome Encapsulated Anti-inflammatory Drugs From the Nasal Region to the Brain. Mol Ther 19(10): 1769-1779.

\* cited by examiner

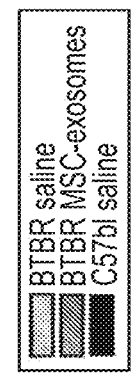
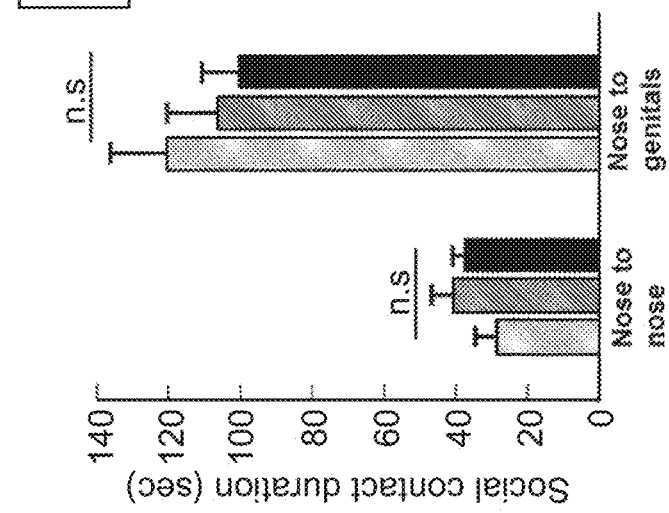
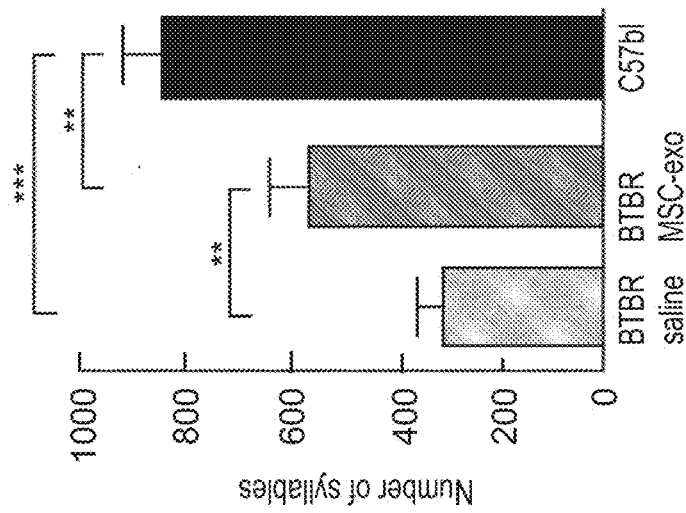
FIG. 2A
FIG. 2B

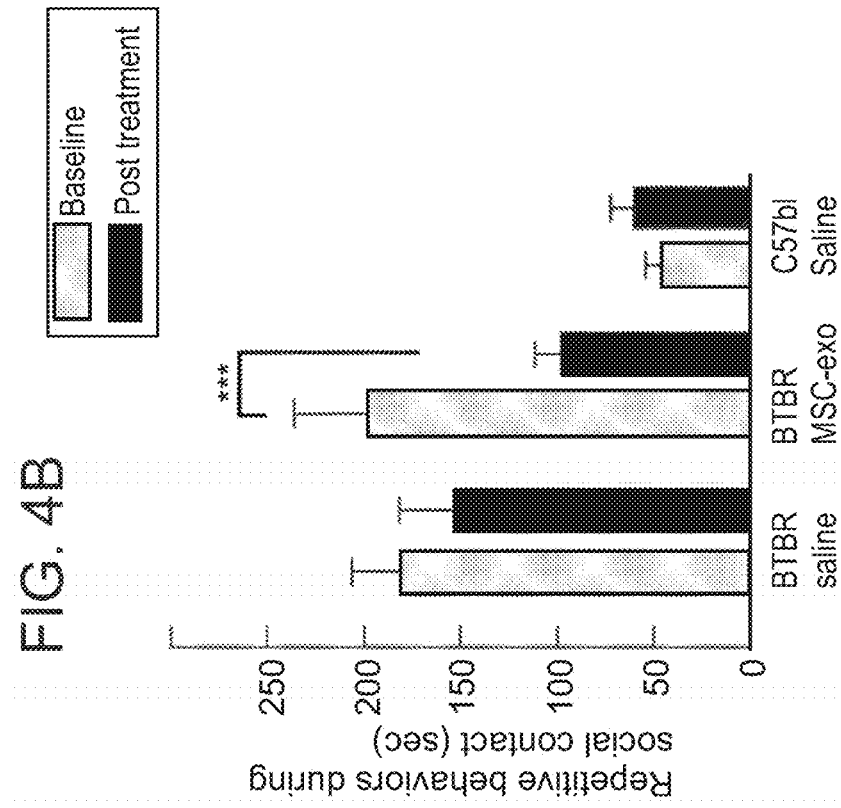
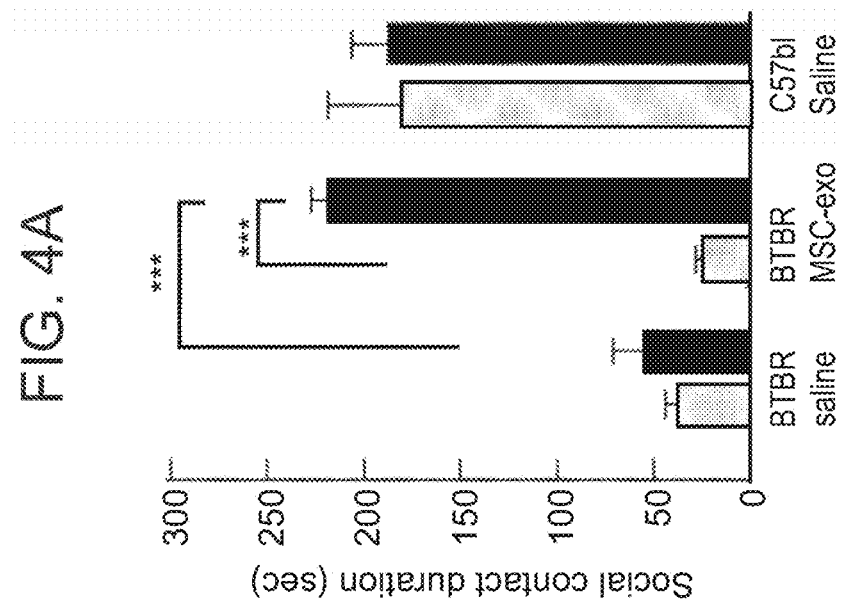

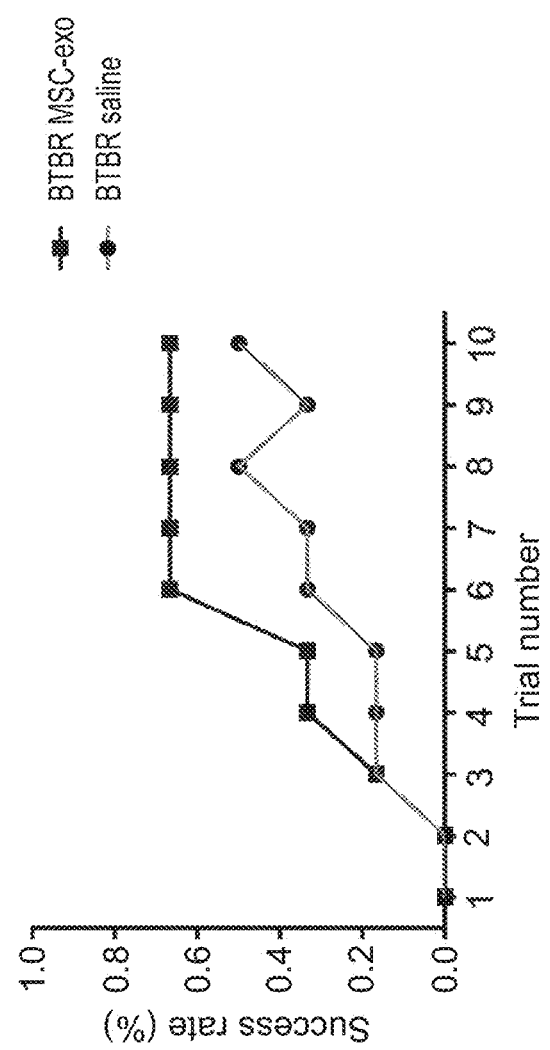
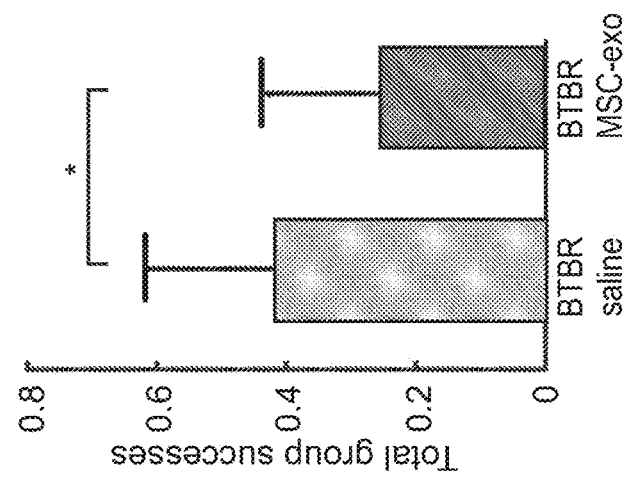

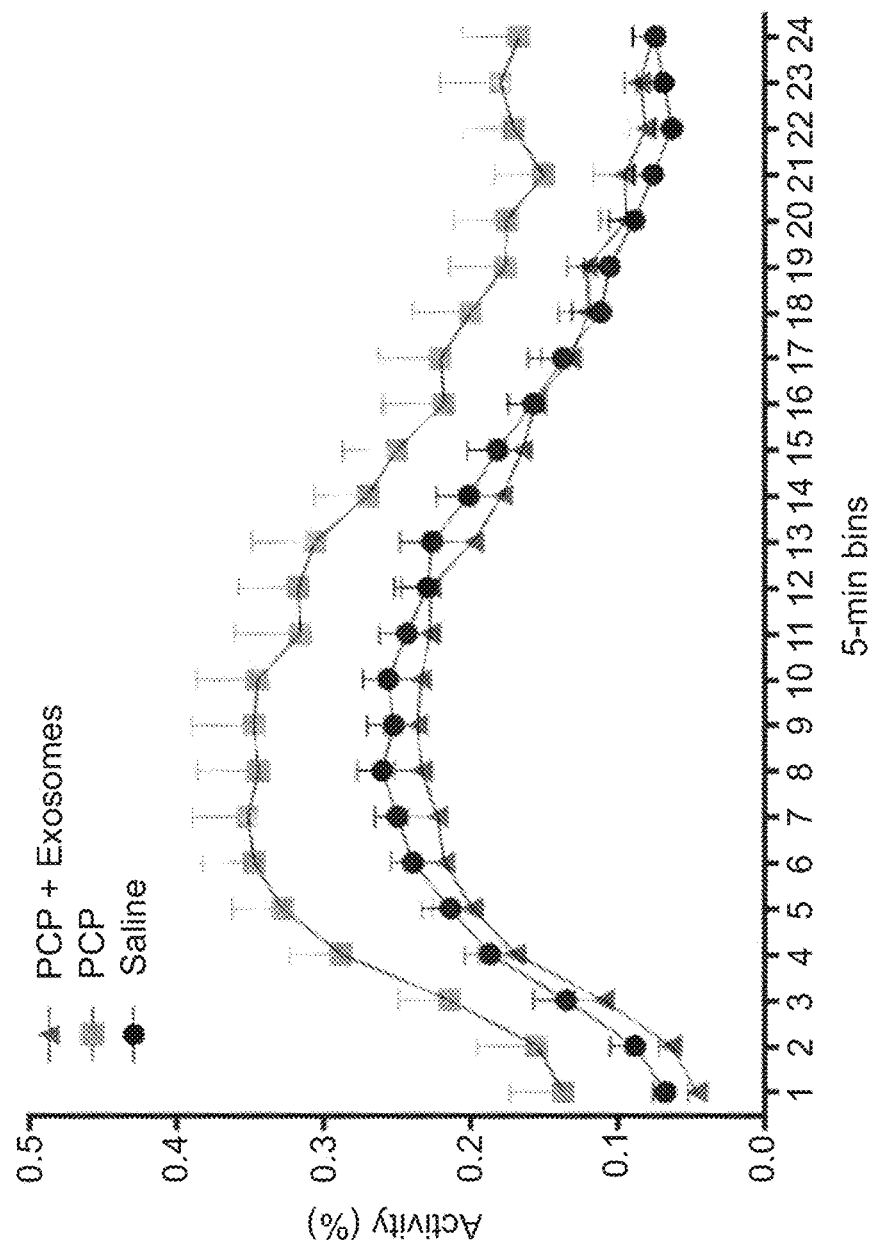

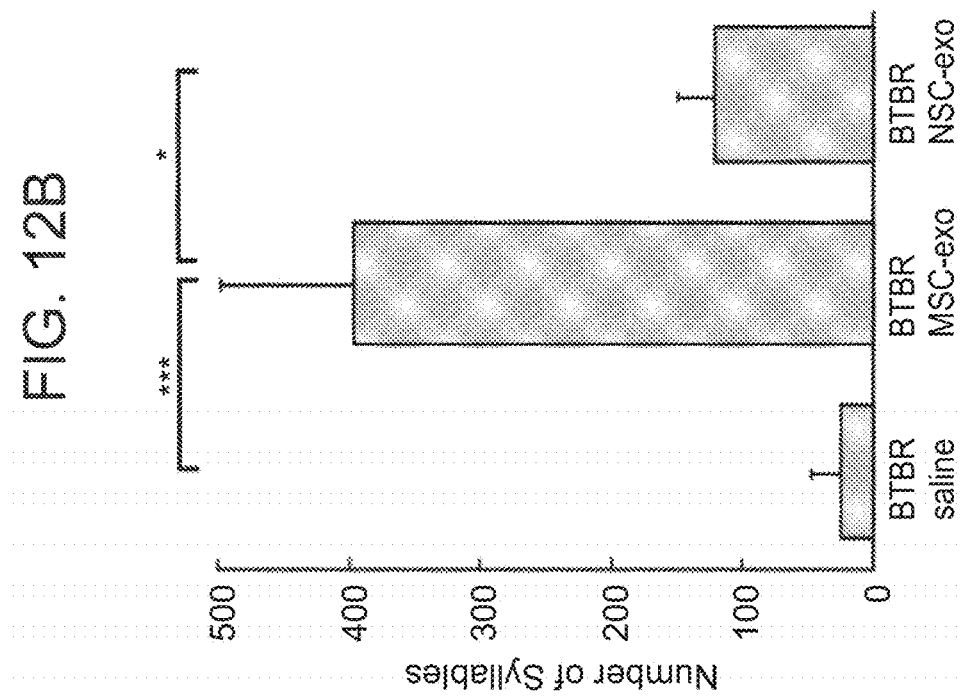

MESENCHYMAL CELL-DERIVED EXOSOMES TO TREAT NEUROLOGICAL DISORDERS

FIELD AND BACKGROUND OF THE INVENTION

The present invention, in some embodiments thereof, relates to particles derived from mesenchymal stem cells for the treatment of neurological disorders and, more particularly, but not exclusively, to Autism.

Autism spectrum disorders (ASD) are neurodevelopmental disabilities characterized by three core symptoms: severe impairment of social interactions and communication skills, increased repetitive behaviors and cognitive inflexibility (Blenner, Reddy, & Augustyn, 2011). Although the pathophysiology underlying ASD is still unclear, recent evidence suggests that various molecular dysfunctions, such as deficits in neurogenesis (Wegiel et al., 2010), neuroimmune processes (Ashwood et al., 2011; Li et al., 2009), and neurotrophic factor availability, (Nickl-Jockschat & Michel, 2011) are involved. BTBR mice are an inbred strand that shows communication and social interaction deficits as well as cognitive inflexibility and increased repetitive behaviors (Bolivar et. Al. 2007). Neurologically, BTBR suffers from decreased hippocampal neurogenesis, which is correlated to autistic humans (Stephenson et. al. 2011). It has been shown that transplantation of MSC to the lateral ventricles of the brain of BTBR mice, adjacent to sub-ventricular zone, have the ability to benefit their autistic-like behaviors, such as increasing interest in unfamiliar male mice, reducing repetitive behaviors and cognitive inflexibility (Segal-Gavish et. al. 2015).

Schizophrenia (SCZ) is a severe neurodevelopmental disorder with a worldwide lifetime risk of approximately 1% and characterized by positive symptoms (e.g. delusions and hallucinations), negative symptoms (e.g. affective flattening, apathy and social withdrawal), and cognitive dysfunction. SCZ is caused by a combination of genetic factors and environmental insults, including prenatal infection, perinatal complication and *cannabis* use. The pathological mechanisms underlying the long time course of SCZ have not yet been fully elucidated. Consequently, current antipsychotic treatments for SCZ have insufficient effect on negative symptoms and the cognitive deficits, which are considered as the core feature of this devastating illness.

Exosomes were initially thought to be a mechanism for removing unneeded membrane proteins from reticulocytes but current studies have shown they are used for cell-to cell communication by carrying genetic information from one cell to another. Several studies have reported that MSC-derived exosomes have functions similar to those of MSCs, such as repairing tissue damage, suppressing inflammatory responses, and modulating the immune system (Yu et. al. 2014). Exosomes are easily traceable and can be targeted to specific areas, which makes it easier to follow their mechanism of action compared to cells (Valadi et. Al. 2007). Furthermore, exosomes have shown to have significant biological effects on the brain when they are administered intranasally, such as decreasing inflammation (Zhuang et. Al. 2011).

US 20150190430 teaches exosomes of MSCs to treat Alzheimer's Disease and Parkinson's.

WO2013150303 teaches exosomes of neural stem cells to treat ND disorders.

Yu et al., Int J Mol Sci. 2014 March; 15(3): 4142-4157 teaches exosomes of MSCs to treat Alzheimer's Disease.

SUMMARY OF THE INVENTION

According to an aspect of the present invention, there is provided a method of treating a neurological disease in a subject comprising administering to the subject a therapeutically effective amount of particles derived from mesenchymal stem cells (MSCs), wherein the neurological disease is not Alzheimer's Disease or Parkinson's Disease, thereby treating the neurological disease in the subject.

According to an aspect of the present invention, there is provided a method of treating an autism spectrum disorder (ASD) in a subject comprising administering to the subject a therapeutically effective amount of microparticles derived from mesenchymal stem cells, thereby treating the autism spectrum disorder.

According to an aspect of the present invention, there is provided a method of treating stroke in a subject in need thereof comprising intranasally administering to the subject a therapeutically effective amount of particles derived from mesenchymal stem cells, thereby treating stroke in the subject.

According to further features in the described preferred embodiments, the neurological disease is schizophrenia.

According to further features in the described preferred embodiments, the administering comprises intranasally administering.

According to further features in the described preferred embodiments, the particles are selected from the group consisting of exosomes, microvesicles, membrane particles, membrane vesicles, ectosomes and exovesicles.

According to further features in the described preferred embodiments, the particles are exosomes.

According to further features in the described preferred embodiments, the particles are microparticles.

According to further features in the described preferred embodiments, the mesenchymal stem cells are derived from dental pulp.

According to further features in the described preferred embodiments, the mesenchymal stem cells are derived from bone marrow.

According to further features in the described preferred embodiments, the MSCs are human MSCs.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-B. Intranasal MSC-exosomes were found in neurons. DAPI-NEUN-PKH26. X60.

FIGS. 4A-B. MSC-exosomes increase male to male social interaction (A) and decrease repetitive behaviors during social interaction (B). Each group was tested for basal behaviors (gray) and was tested again 3 weeks after treatment (saline or MSC-exo, black). BTBR MSC-exo was the only group that had significant difference before and after treatment in time spent in social interaction and in repetitive behaviors during social interaction (paired T-test, SEM). BTBR MSC-exo was significantly different from C57bl saline group before treatment and significantly different from BTBR saline group (ANOVA1, SEM). ***$p<0.001$.

FIGS. 6A-B. MSC-Exosomes decrease cognitive rigidity. BTBR-exo mice were more likely to learn the reversal of the Water T-Maze Assay and less likely to revert into the pattern learned on the first and second days (A). BTBR-exo mice were quicker in their learning, having 4 mice learn to consistently go on the reversal path by the 6th trial. The BTBR-saline mice took more time to learn and were less likely to consistently turn the correct way. After 10 trials, 3 of the 6 BTBR-saline mice had learned the new path but only 2 of them could follow it reliably. Comparison between groups at each single trial is not significant, but the total number of correct turns is significantly higher in the MSC-exo group compared to saline group and the difference between the total group success is significant (B), (t=0.026).

FIGS. 8A-B are graphs illustrating that MSC-exosome treated mice had reduced activity following PCP injection as compared to control.

FIG. 12B is a graph illustrating that there is a significant improvement of ultrasonic vocalizations after intranasal administration of MSC-exo. NSC-exo were not effective.

DESCRIPTION OF SPECIFIC EMBODIMENTS OF THE INVENTION

The present invention, in some embodiments thereof, relates to particles derived from mesenchymal stem cells for the treatment of neurological disorders and, more particularly, but not exclusively, to autism.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Exosomes were initially thought to be a mechanism for removing unneeded membrane proteins from reticulocytes. However, recent studies have shown they are also used for cell-to cell communication through the carrying of genetic information from one cell to another. Exosomes contain mainly proteins, as well as RNA and a large number of micro RNAs. Approximately 25 percent of these proteins and RNA play role in cell growth and maintenance.

The present inventors investigated whether mesenchymal stem cell-derived exosomes have a beneficial effect on neurological diseases.

In the first case, the inventors investigated the effect of mesenchymal stem cell-derived exosomes on autism using the inbred mouse strain BTBR T1tf/J (BTBR) which incorporates multiple behavioral phenotypes relevant to the three diagnostic symptoms of autism—severe impairment of social interactions and communication skills, increased repetitive behaviors, and cognitive inflexibility. BTBR mice present with a selectively reduced social approach, low reciprocal social interactions, and impaired juvenile play in comparison to the C57BL controls.

Figure 3A:
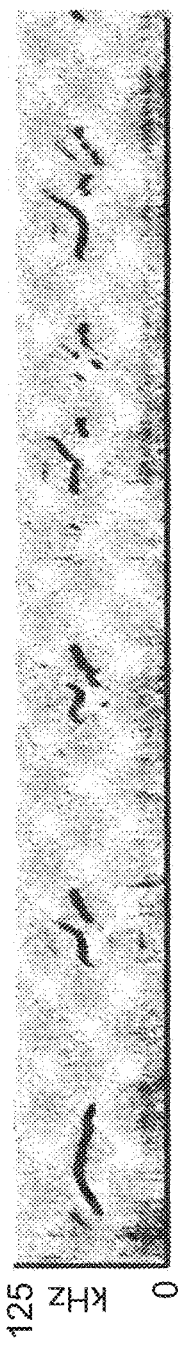
FIGS. 3A-C. Specific improvement of ultrasonic vocalizations after intranasal administration of MSC-exosomes. A. BTBR MSC-exo had more syllables of ultrasonic vocalizations compared to saline BTBR. B. No significant difference between the groups in social contact (nose to nose and nose to genitals), suggesting specific effect on ultrasonic vocalizations. C. visualization of typical syllables of each group. BTBR MSC-exo became closer to C57bl in features of syllable duration and complexity. $p<0.01$, *$p<0.001$, SEM.
Figure 3B:
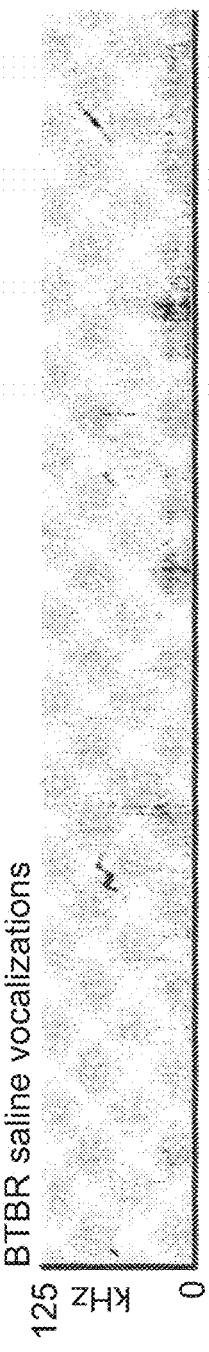
Figure 3C:
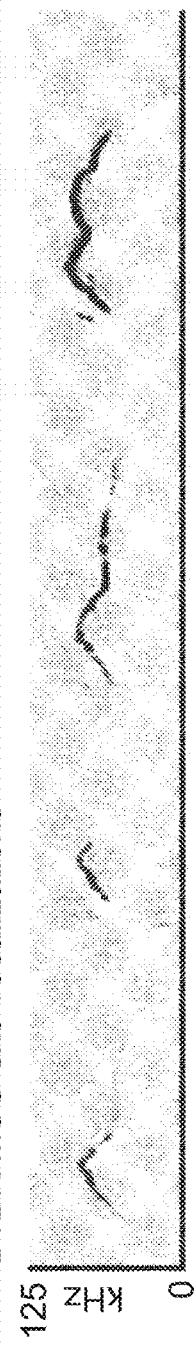
Figure 5:
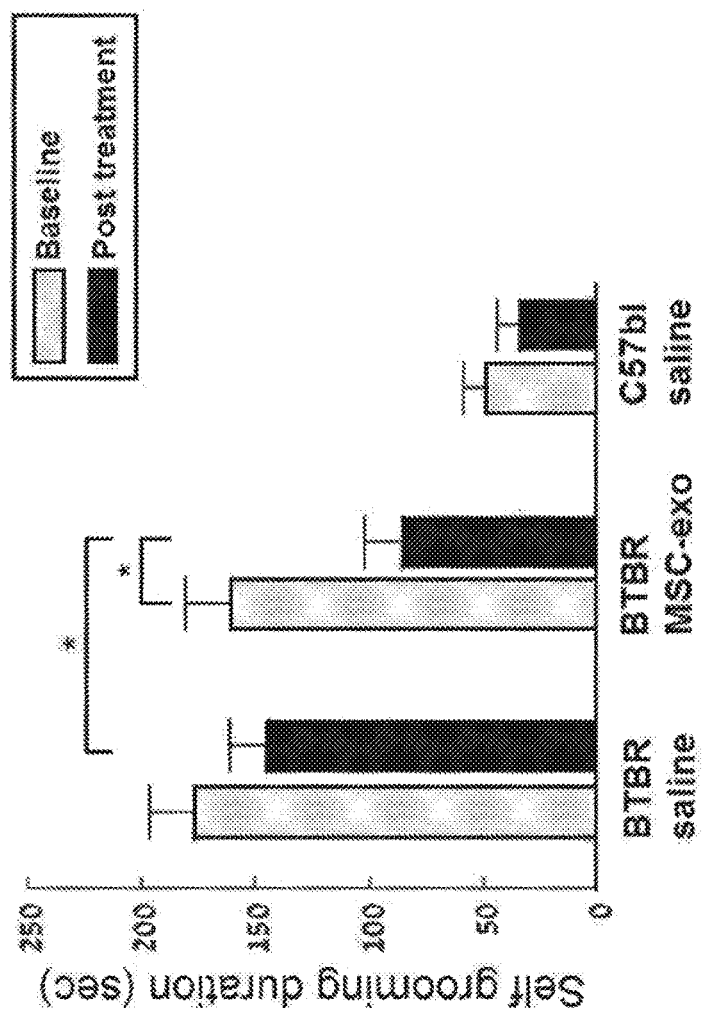
FIG. 5. MSC-exosomes decrease repetitive behavior of self-grooming. Each group was tested for basal behaviors (gray) and was tested again 3 weeks after treatment (saline or MSC-exo, black). BTBR MSC-exo was the only group that had significant difference before and after treatment in the time spent self-grooming (paired T-test, SEM). BTBR MSC-exo was significantly different from C57bl saline group before treatment and significantly different from BTBR saline group (ANOVA1, SEM). *$p<0.05$.

The present inventors have shown that mice with intranasal administration of mesenchymal stem cell-derived exosomes (also referred to herein as MSC-exo) present significant improvement in the social interaction domain. Male BTBR mice treated with MSC-derived exosomes presented increased social interest in other stranger males compared to their own baseline behaviors before the treatment and compared to other saline treated males (FIGS. 4A-B). Their time spent in social interaction was comparable to c57bl group. In male to female ultrasonic vocalization (USV) communication, mice treated with MSC-exo had significantly higher number of USVs compared to saline treated group toward the female (FIGS. 3A-C). Second core symptom of autistic-like behavior of BTBR mice is increased time spent in repetitive behaviors of digging and grooming. Here the present inventors show that mice treated with MSC-derived exosomes spent less time, compared to their baseline, in repetitive behaviors during social interaction and while isolated (FIG. 5). The third core symptom of autistic-like behaviors of BTBR mice, the cognitive rigidity. The present inventors show that MSC-derived exosome treated mice had significantly fewer mistakes during the reversal condition of the rescue platform compared to saline treated group during the water T-maze assay (FIGS. 6A-B).

Figure 7:
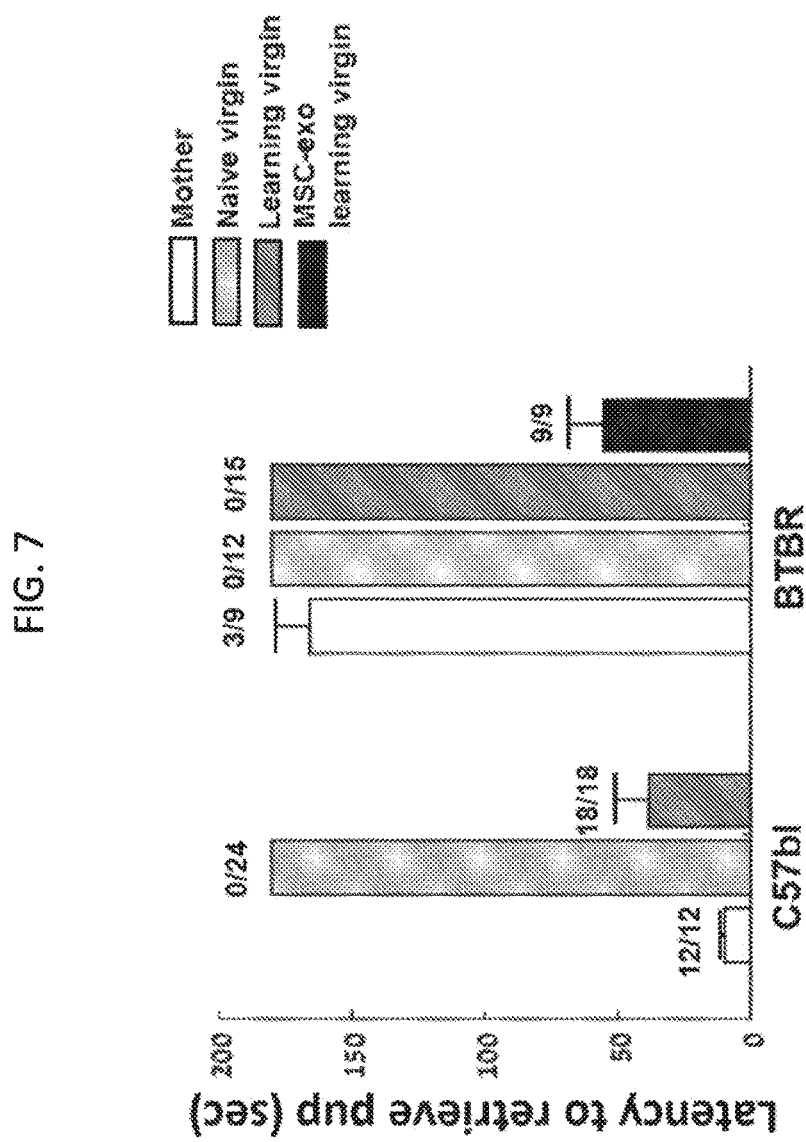
FIG. 7. MSC-exosomes improve learning of maternal behaviors. C57bl mothers collected all the pups to a shelter in average of 9.9 seconds (C57bl, white), naïve virgins do not collect any of the pups after 180 seconds (c57bl, pale gray) and virgins that spent 3 days with C57BL mother learned to collect all the pups in an average of 37 seconds (C5bl, dark gray). BTBR mothers with saline administration did not collect most of the pups after 180 seconds. BTBR naïve virgins did not collect any of the pups after 180 seconds. BTBR MSC-exo, after spending 2 days with BTBR saline mother, collected all the pups in average of 55 seconds (SEM).

The present inventors have also examined the effect of MSC-derived exosomes on pup retrieval behavior. It is known that after giving birth, a mother makes a nest for the new-born pups and when pups are isolated the mother immediately retrieves it and brings it back to the nest. A naïve virgin female will not retrieve the isolated pup, but if the virgin spends a few days with the mother, the virgin can learn pup retrieval behavior thus becoming experienced virgin (Marlin, Mitre, D'amour, Chao, & Froemke, 2015). Here, the present inventors show that neither the BTBR mothers nor BTBR experienced virgin present baseline behavior of pup retrieval as c57bl mothers do. However, when treated with MSC-derived exosomes, BTBR experienced virgins have the same pup retrieval behaviors as c57bl experienced virgins (FIG. 7).

In the second case, the inventors investigated the effect of mesenchymal stem cell-derived exosomes on schizophrenia using a pharmacological rodent model based on phencyclidine (PCP), which acts as a NMDA glutamate receptor antagonist.

Figure 8B:
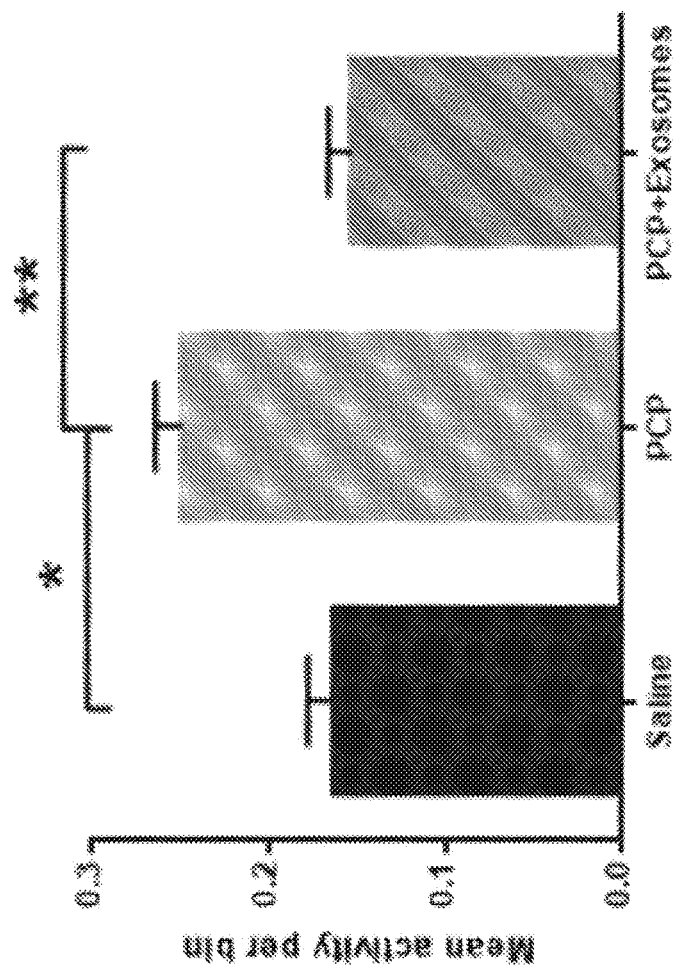
Figure 9:
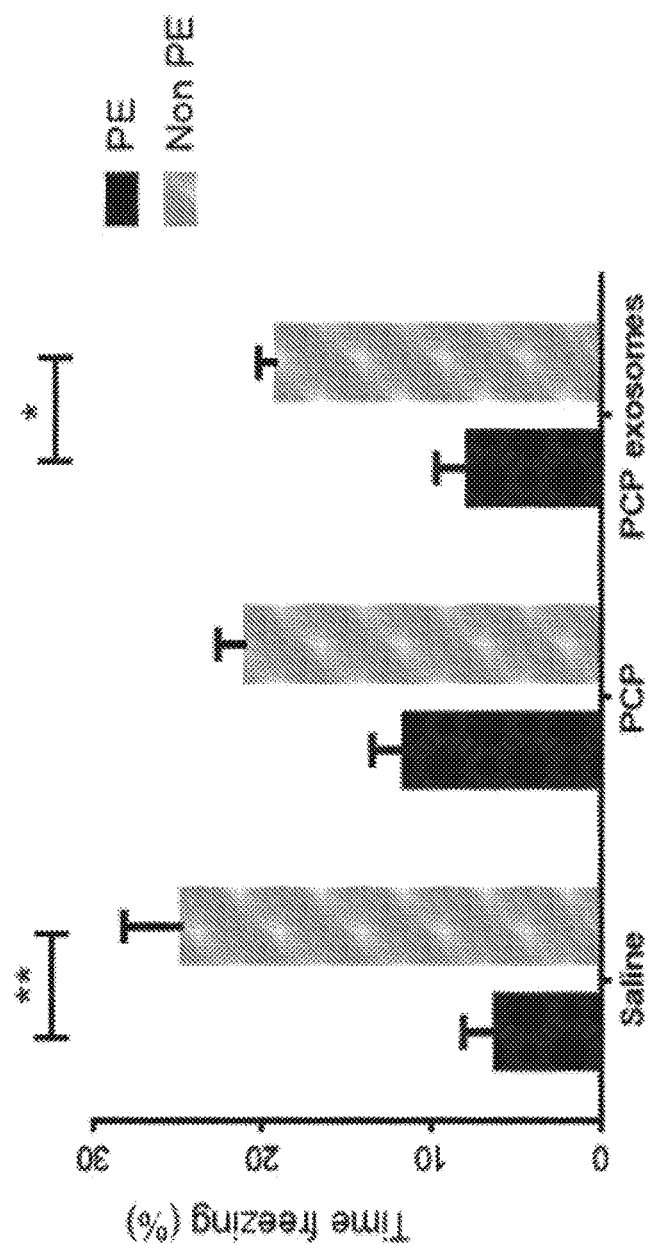
FIG. 9 is a graph illustrating the effects of PCP subchronic treatment on central information processing. The bar plot show percent time freezing in non-pre-exposed (NPE) and pre-exposed (PE) subjects during the tone CS during conditioning phase of the latent inhibition task. Symbols (*) and (**) refer to a statistical significance of $P<0.05$ and $P<0.01$ respectively. All values are mean±SEM.
Figure 10:
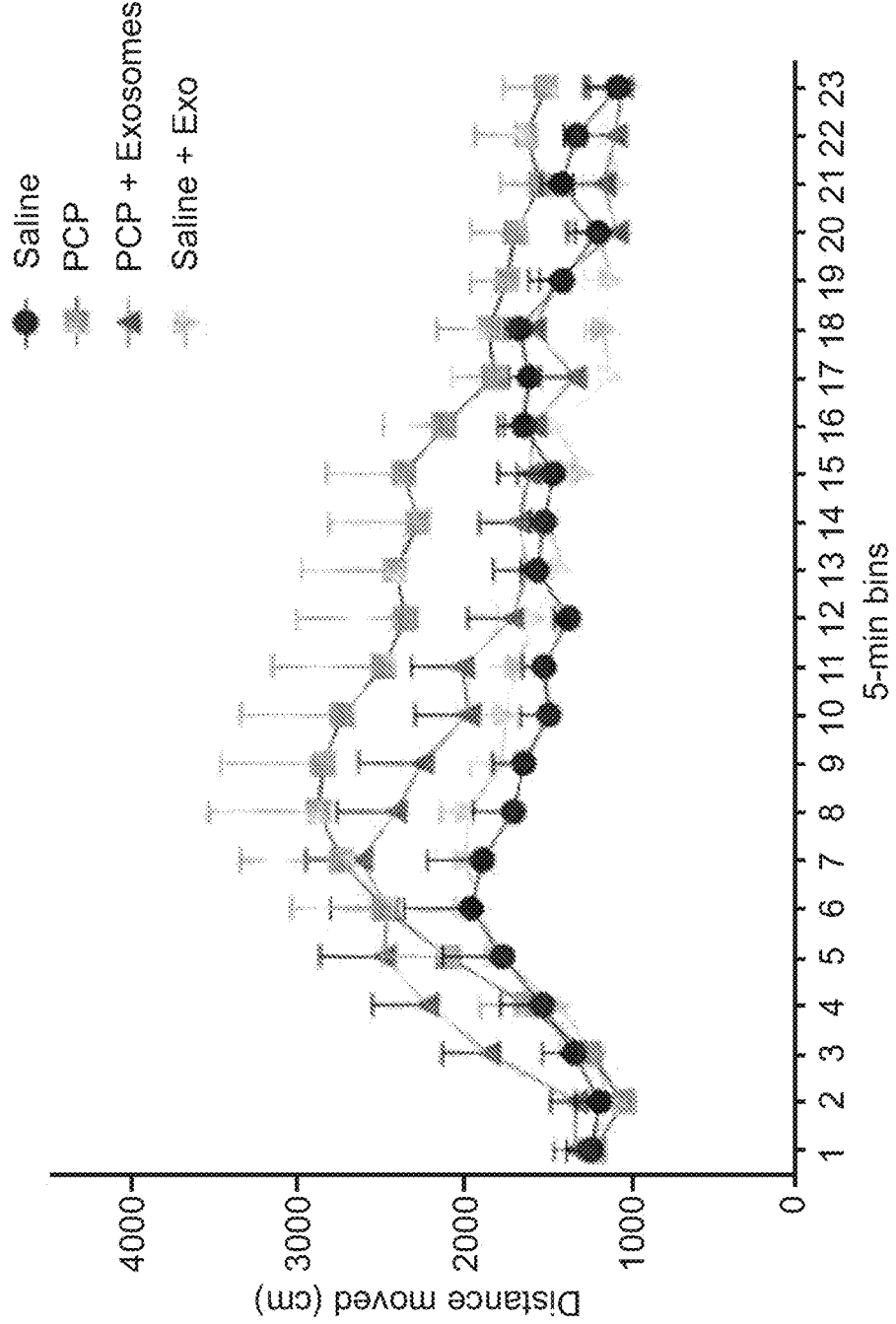
FIG. 10 is a graph illustrating the effects of PCP subchronic treatment on the susceptibility to systemic amphetamine (2.5 mg/kg, i.p.). PCP treatment increased the locomotor response to systemic amphetamine as measured by the distance moved (in cm) of mice in the open field. Statistical significance was illustrated only after the 40-min peak in activity.
Figure 11:
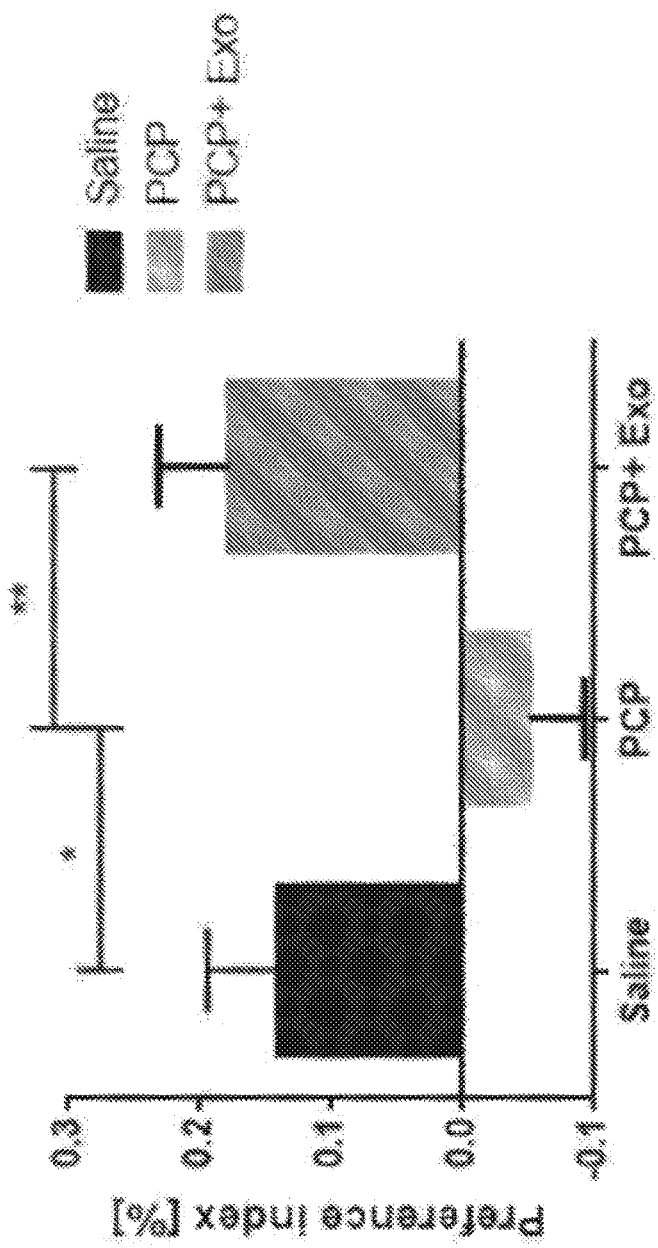
FIG. 11 is a graph illustrating the results of a three chamber social approach test. Time spent in close proximity to the social cage and the non-social cage were measured. Presented is the preference index, indicating the amount of time spent in close proximity to the social stimulus relative to the time spend near both social and non-social stimuli. Symbols (*) and (**) refer to a statistical significance of $P<0.05$ and $P<0.01$ respectively. All values are mean±SEM.

FIGS. 8A-B and 10 illustrate that mice treated with mesenchymal stem cell-derived exosomes showed a reduced locomotor response to systemic amphetamine administration when administered with PCP. FIG. 9 illustrates the positive effect of the MSC-derived exosomes on central information processing in PCP-treated mice, analyzed by assessing the acoustic startle reflex. Furthermore, the exosome treated mice showed the highest preference for the social stimulus in this model (FIG. 11).

Altogether, the present inventors have demonstrated the positive effect of mesenchymal stem cell-derived exosomes in two neurological disorders with very different etiologies. Accordingly, the present inventors propose that mesenchymal stem cell-derived exosomes will serve as a useful therapeutic for neurological diseases in general.

Thus, according to a first aspect of the present invention, there is provided a method of treating a neurological disease in a subject comprising administering to the subject a therapeutically effective amount of particles derived from mesenchymal stem cells, wherein the neurological disease is not Alzheimer's Disease or Parkinson's Disease, thereby treating the neurological disease in the subject.

The term "mesenchymal stem cells" refers to multipotent stromal cells that can differentiate into a variety of cell types, including: osteoblasts (bone cells), chondrocytes (cartilage cells), myocytes (muscle cells) and adipocytes (fat cells). In their pluripotent state, mesenchymal stem cells typically express the following markers: CD105, CD166, CD29, CD90, and CD73, and do not express CD34, CD45, and CD133.

Mesenchymal stem cells may be isolated from a variety of tissues including but not limited to bone marrow, adipose tissue, dental pulp, oral mucosa, peripheral blood and amniotic fluid.

Methods of isolating, purifying and expanding mesenchymal stem cells (MSCs) are known in the arts and include, for example, those disclosed by Caplan and Haynesworth in U.S. Pat. No. 5,486,359 and Jones E. A. et al., 2002, Isolation and characterization of bone marrow multipotential mesenchymal progenitor cells, Arthritis Rheum. 46(12): 3349-60.

Preferably, mesenchymal stem cell cultures are generated by diluting BM aspirates (usually 20 ml) with equal volumes of Hank's balanced salt solution (HBSS; GIBCO Laboratories, Grand Island, N.Y., USA) and layering the diluted cells over about 10 ml of a Ficoll column (Ficoll-Paque; Pharmacia, Piscataway, N.J., USA). Following 30 minutes of centrifugation at 2,500×g, the mononuclear cell layer is removed from the interface and suspended in HBSS. Cells are then centrifuged at 1,500×g for 15 minutes and resuspended in a complete medium (MEM, α medium without deoxyribonucleotides or ribonucleotides; GIBCO); 20% fetal calf serum (FCS) derived from a lot selected for rapid growth of MSCs (Atlanta Biologicals, Norcross, Ga.); 100 units/ml penicillin (GIBCO), 100 μg/ml streptomycin (GIBCO); and 2 mM L-glutamine (GIBCO). Resuspended cells are plated in about 25 ml of medium in a 10 cm culture dish (Corning Glass Works, Corning, N.Y.) and incubated at 37° C. with 5% humidified $CO_2$. Following 24 hours in culture, nonadherent cells are discarded, and the adherent cells are thoroughly washed twice with phosphate buffered saline (PBS). The medium is replaced with a fresh complete medium every 3 or 4 days for about 14 days. Adherent cells are then harvested with 0.25% trypsin and 1 mM EDTA (Trypsin/EDTA, GIBCO) for 5 min at 37° C., replated in a 6-cm plate and cultured for another 14 days. Cells are then trypsinized and counted using a cell counting device such as for example, a hemocytometer (Hausser Scientific, Horsham, Pa.). Cultured cells are recovered by centrifugation and resuspended with 5% DMSO and 30% FCS at a concentration of 1 to $2 \times 10^6$ cells per ml. Aliquots of about 1 ml each are slowly frozen and stored in liquid nitrogen.

To expand the mesenchymal stem cell fraction, frozen cells are thawed at 37° C., diluted with a complete medium and recovered by centrifugation to remove the DMSO. Cells are resuspended in a complete medium and plated at a concentration of about 5,000 cells/cm². Following 24 hours in culture, nonadherent cells are removed and the adherent cells are harvested using Trypsin/EDTA, dissociated by passage through a narrowed Pasteur pipette, and preferably replated at a density of about 1.5 to about 3.0 cells/cm². Under these conditions, MSC cultures can grow for about 50 population doublings and be expanded for about 2000 fold [Colter D C., et al. Rapid expansion of recycling stem cells in cultures of plastic-adherent cells from human bone marrow. Proc Natl Acad Sci USA. 97: 3213-3218, 2000].

MSC cultures utilized by some embodiments of the invention preferably include three groups of cells which are defined by their morphological features: small and agranular cells (referred to as RS-1, hereinbelow), small and granular cells (referred to as RS-2, hereinbelow) and large and moderately granular cells (referred to as mature MSCs, hereinbelow). The presence and concentration of such cells in culture can be assayed by identifying a presence or absence of various cell surface markers, by using, for example, immunofluorescence, in situ hybridization, and activity assays.

As mentioned, the present invention contemplates using particles derived from mesenchymal stem cells for treating neurological diseases.

The term "particle" as used herein refers to a discrete entity that incorporates biological matter such as proteins and/or RNA. It will be appreciated that particle of this aspect of the present invention is not a biological cell.

The particle may be derivable from the MSC by any of several means, for example by secretion, budding or dispersal from the MSC. For example, the particle may be produced, exuded, emitted or shed from the MSC. Where the MSC is in cell culture, the particle may be secreted into the cell culture medium.

The particle may in particular comprise a vesicle. The particle may comprise an exosome. The particles described here may comprise any one or more of the properties of the exosomes described herein.

The particle may comprise a vesicle or a flattened sphere limited by a lipid bilayer. The particles may comprise diameters of 40-100 nm. The particles may be formed by inward budding of the endosomal membrane. The particles may have a density of .about. 1.13-1.19 g/ml and may float on sucrose gradients. The particles may be enriched in cholesterol and sphingomyelin, and lipid raft markers such as GM1, GM3, flotillin and the src protein kinase Lyn. The particles may comprise one or more proteins present in mesenchymal stem cells or mesenchymal stem cell conditioned medium (MSC-CM), such as a protein characteristic or specific to the MSC or MSC-CM. They may comprise RNA, for example miRNA.

According to a particular embodiment, the particle is an exosome.

As used herein, the term "exosome" refers to an extracellular vesicle that is released from a cell upon fusion of a multivesicular body (MVB) with the plasma membrane.

The exosome may (a) have a size of between 50 nm and 100 nm as determined by electron microscopy; (b) comprises a complex of molecular weight>100 kDa, comprising proteins of <100 kDa; (c) comprises a complex of molecular weight>300 kDa, comprising proteins of <300 kDa; (d) comprises a complex of molecular weight>1000 kDa; (e) has a size of between 2 nm and 200 nm, as determined by filtration against a 0.2 pM filter and concentration against a membrane with a molecular weight cut-off of 10 kDa; or (f) a hydrodynamic radius of below 100 nm, as determined by laser diffraction or dynamic light scattering.

The particle may be something that is isolatable from a mesenchymal stem cell (MSC) or mesenchymal stem cell conditioned medium (MSC-CM). The particle may be responsible for at least an activity of the MSC or MSC-CM. The particle may be responsible for, and carry out, substantially most or all of the functions of the MSC or MSC-CM. For example, the particle may be a substitute (or biological substitute) for the MSC or MSC-CM.

The particle preferably has at least one property of a mesenchymal stem cell. The particle may have a biological property, such as a biological activity. The particle may have any of the biological activities of an MSC. The particle may for example have a therapeutic or restorative activity of an MSC.

The particle may be produced or isolated in a number of ways. Such a method may comprise isolating the particle from a mesenchymal stem cell (MSC). Such a method may comprise isolating the particle from a mesenchymal stem cell conditioned medium (MSC-CM).

The particle may be isolated for example by being separated from non-associated components based on any property of the particle. For example, the particle may be isolated based on molecular weight, size, shape, composition or biological activity.

The conditioned medium may be filtered or concentrated or both during, prior to or subsequent to separation. For example, it may be filtered through a membrane, for example one with a size or molecular weight cut-off. It may be subject to tangential force filtration or ultrafiltration.

For example, filtration with a membrane of a suitable molecular weight or size cutoff, as described in the Assays for Molecular Weight elsewhere in this document, may be used.

The conditioned medium, optionally filtered or concentrated or both, may be subject to further separation means, such as column chromatography. For example, high performance liquid chromatography (HPLC) with various columns may be used. The columns may be size exclusion columns or binding columns.

One or more properties or biological activities of the particle may be used to track its activity during fractionation of the mesenchymal stem cell conditioned medium (MSC-CM). As an example, light scattering, refractive index, dynamic light scattering or UV-visible detectors may be used to follow the particles. For example, a therapeutic activity such as cardioprotective activity may be used to track the activity during fractionation.

The following paragraphs provide a specific example of how a mesenchymal stem cell particle such as an exosome may be obtained.

A mesenchymal stem cell particle may be produced by culturing mesenchymal stem cells in a medium to condition it. The medium may comprise DMEM. The DMEM may be such that it does not comprise phenol red. The medium may be supplemented with insulin, transferrin, or selenoprotein (ITS), or any combination thereof. It may comprise FGF2. It may comprise PDGF AB. The concentration of FGF2 may be about 5 ng/ml FGF2. The concentration of PDGF AB may be about 5 ng/ml. The medium may comprise glutamine-penicillin-streptomycin or -mercaptoethanol, or any combination thereof.

The cells may be cultured for about 1, 2, 3, 4, 5, 6, 7, 8, 9, 10 days or more, for example 3 days. The conditioned medium may be obtained by separating the cells from the medium. The conditioned medium may be centrifuged, for example at 500 g. it may be concentrated by filtration through a membrane. The membrane may comprise a >1000 kDa membrane. The conditioned medium may be concentrated about 50 times or more.

The conditioned medium may be subject to liquid chromatography such as HPLC. The conditioned medium may be separated by size exclusion. Any size exclusion matrix such as Sepharose may be used. As an example, a TSK Guard column SWXL, 6×40 mm or a TSK gel G4000 SWXL, 7.8×300 mm may be employed. The eluent buffer may comprise any physiological medium such as saline. It may comprise 20 mM phosphate buffer with 150 mM of NaCl at pH 7.2. The chromatography system may be equilibrated at a flow rate of 0.5 ml/min. The elution mode may be isocratic. UV absorbance at 220 nm may be used to track the progress of elution. Fractions may be examined for dynamic light scattering (DLS) using a quasi-elastic light scattering (QELS) detector.

Fractions which are found to exhibit dynamic light scattering may be retained. For example, a fraction which is produced by the general method as described above, and which elutes with a retention time of 11-13 minutes, such as 12 minutes, is found to exhibit dynamic light scattering. The r.sub.h of particles in this peak is about 45-55 nm. Such fractions comprise mesenchymal stem cell particles such as exosomes.

The particle may have a size of greater than 2 nm. The particle may have a size of greater than 5 nm, 10 nm, 20 nm, 30 nm, 40 nm or 50 nm. The particle may have a size of greater than 100 nm, such as greater than 150 nm. The particle may have a size of substantially 200 nm or greater.

The particle or particles may have a range of sizes, such as between 2 nm to 20 nm, 2 nm to 50 nm, 2 nm to 100 nm, 2 nm to 150 nm or 2 nm to 200 nm. The particle or particles may have a size between 20 nm to 50 nm, 20 nm to 100 nm, 20 nm to 150 nm or 20 nm to 200 nm. The particle or particles may have a size between 50 nm to 100 nm, 50 nm to 150 nm or 50 nm to 200 nm. The particle or particles may have a size between 100 nm to 150 nm or 100 nm to 200 nm. The particle or particles may have a size between 150 nm to 200 nm.

The size may be determined by various means. In principle, the size may be determined by size fractionation and filtration through a membrane with the relevant size cut-off. The particle size may then be determined by tracking segregation of component proteins with SDS-PAGE or by a biological assay.

The size may comprise a hydrodynamic radius. The hydrodynamic radius of the particle may be below 100 nm. It may be between about 30 nm and about 70 nm. The hydrodynamic radius may be between about 40 nm and about 60 nm, such as between about 45 nm and about 55 nm. The hydrodynamic radius may be about 50 nm.

The hydrodynamic radius of the particle may be determined by any suitable means, for example, laser diffraction or dynamic light scattering.

The particle may comprise one or more proteins or polynucleotides secreted by a mesenchymal stem cell. The particle may comprise one or more proteins or polynucleotides present in mesenchymal stem cell conditioned medium (MSC-CM). In a particular embodiment, the particle may comprise miRNAs which are derived from MSCs.

For example, the particle may comprise 10% or more, 20% or more, 30% or more, 40% or more, 50% or more, 60% or more or 70% or more of these proteins and/or polynucleotides. The particle may comprise substantially about 75% of these proteins and/or polynucleotides. The proteins may be defined by reference to a list of proteins or gene products of a list of genes.

As mentioned, the particles of this aspect of the present invention are useful for treating neurological diseases.

Subjects that may be treated include mammalian subjects, such as humans, mice, rats, monkeys, dogs and cats.

The term "neurological disease" refers to a disease of the brain, spine and/or the nerves that connect them.

According to one embodiment, the disease is a memory disease.

In a preferred embodiment, the disease is a neurodevelopmental disorder such as autism or schizophrenia.

According to another embodiment, the disease is a behavioral disease such as schizophrenia, attention deficit hyperactivity disorder, autism, Tourette's syndrome, obsessive compulsive disorder, as well as the neurobehavioral associated symptoms of degeneratives of the nervous system such as Parkinson's disease, essential tremor, Huntington's disease, Alzheimer's disease, multiple sclerosis and organic psychosis.

In one embodiment, the neurological disease is not Parkinson's Disease or Alzheimer's disease (AD).

In another embodiment, the neurological disease is not stroke.

According to a particular embodiment, the neurological disease is an autism spectrum disorder (ASD).

As mentioned, the particles of embodiments of this invention can be used for preparing a medicament (interchangeably referred to as pharmaceutical composition), whereby such a medicament is formulated for treating neurological diseases.

The particles of the present invention can be administered to the treated individual using a variety of transplantation approaches, the nature of which depends on the site of implantation.

The term or phrase "transplantation", "cell replacement" or "grafting" injection are used interchangeably herein and refer to the introduction of the particles of the present invention to target tissue, such as the brain, the grey matter etc. The mesenchymal stem cells from where the particles are obtained can be derived from the recipient (allogeneic) or from a non-allogeneic or xenogeneic donor.

The particles can be transplanted directly into the spinal cord (intrathecally), intravenously, directly into the brain or combinations of same such that it reaches the brain. In one embodiment, the particles are delivered non-invasively, e.g. intranasally. Other modes of administration are also contemplated such as systemic administration.

An exemplary dose of particles (e.g. exosomes) that may be administered (e.g. intranasally) per treatment may be between $1\times10^6$-$1\times10^{20}$ and more preferably between $1\times10^9$-$1\times10^{15}$ for a 70 kg human.

In any of the methods described herein, the particles can be administered either per se or, preferably as a part of a pharmaceutical composition that further comprises a pharmaceutically acceptable carrier.

As used herein a "pharmaceutical composition" refers to a preparation of the particles described herein, with other chemical components such as pharmaceutically suitable carriers and excipients. The purpose of a pharmaceutical composition is to facilitate administration of the particles to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol; saline; emulsions; buffers; culture medium such as DMEM or RPMI; hypothermic storage medium containing components that scavenge free radicals, provide pH buffering, oncotic/osmotic support, energy substrates and ionic concentrations that balance the intracellular state at low temperatures; and mixtures of organic solvents with water.

Typically, the pharmaceutical carrier preserves the number of particles (e.g. is not reduced by more than 90%) in the composition for at least 24 hours, at least 48 hours or even at least 96 hours.

Herein the term "excipient" refers to an inert substance added to a pharmaceutical composition to further facilitate administration of a compound and maintain cells viability at a pre-determined temperature for a suitable period of time before transplantation/injection. Examples, without limitation, of excipients include albumin, plasma, serum and cerebrospinal fluid (CSF), antioxidants such as N-Acetylcysteine (NAC) or resveratrol.

According to a preferred embodiment of the present invention, the pharmaceutical carrier is an aqueous solution of buffer or a culture medium such as DMEM.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals.

The data obtained from these in vitro and cell culture assays and animal studies can be used in formulating a range of dosage for use in human. Further information may be obtained from clinical studies—see for example Salem H K et al., Stem Cells 2010; 28:585-96; and Uccelli et al. Lancet Neurol. 2011; 10:649-56).

The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1).

For injection, the active ingredients of the pharmaceutical composition may be formulated in aqueous solutions, preferably in physiologically compatible buffers such as Hank's solution, Ringer's solution, or physiological salt buffer and additional agents as described herein above.

Dosage amount and interval may be adjusted individually to levels of the active ingredient which are sufficient to effectively treat the neurological disorder. Dosages necessary to achieve the desired effect will depend on individual characteristics and route of administration.

Depending on the severity and responsiveness of the condition to be treated, dosing of particles can be of a single or a plurality of administrations, with course of treatment lasting from several days to several weeks or months depending when diminution of the disease state is achieved.

The amount of particles to be administered will, of course, be dependent on the individual being treated, the severity of the affliction, the manner of administration, the judgment of the prescribing physician, etc. The dosage and timing of administration will be responsive to a careful and continuous monitoring of the individual changing condition.

Following administration, the particles may be tracked in order to ensure they have reached the target site. This may be carried out using gold nanoparticle for instance—see WO 2013186735 A3.

The particles of the present invention, in at least some embodiments, may be prepackaged in unit dosage forms in a syringe ready for use. The syringe may be labeled with the name of the particles and their source. The labeling may also comprise information related to the function of the particles. The syringe may be packaged in a packaging which is also labeled with information regarding the particles.

The particles of the present invention, in at least some embodiments, may be co-administered with therapeutic agents useful in treating neurological disorders, such as gangliosides; antibiotics, neurotransmitters, neurohormones, toxins, neurite promoting molecules; and antimetabolites small molecule agents and precursors of neurotransmitter molecules such as L-DOPA. Additionally, or alternatively, the particles of the present invention, in at least some embodiments, may be co-administered with other cells capable of alleviating at least one symptom of the neurological disease.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

MSC-Derived Exosomes for Treating Autism

Materials and Methods

Mesenchymal Stem Cell (MSC) Preparation:

Human MSCs were purchased from Lonza (Basel, Switzerland). Cells were cultured and expanded as previously described (Sadan et al., 2012).

Purification Protocol:

The exosomes were purified by taking the culture fluid and centrifuging it for 10 minutes at 300 g. The supernatant was recovered and centrifuged for 10 minutes at 2000 g. Once again, the supernatant was recovered and centrifuged for 30 minutes at 10000 g. The supernatant was taken, put through a 0.22 um filter and centrifuged for 70 minutes at 100000 g. The pellet, containing the exosomes and proteins, was washed in PBS then centrifuged for 70 minutes at 100000 g. The pellet, containing the purified exosomes, was re-suspended in 200 ul of sterilized PBS. Each centrifugation occurred at 4 degrees Celsius.

Number of particles administered per mouse=$8.5 \times 10^9 \, particles/ul$

Staining Protocol:

Stock solution was created by mixing 2 ul pKH 26 in 500 ul diluent. From the stock, 100 ul was added to 50 ul of exosomes in PBS. After 5 minutes, 100 ul of exosome-free platelets was added to the previous mixture then centrifuged for 90 minutes at 100 g at 4 degrees Celsius. The pellet was resuspended in 200 ul of PBS. Whole brain fluorescence imaging was taken with Maestro CRi, excitation filter 523 and emission filter 560.

Animals:

BTBR T1tf/J mice were bred from adult pairs originally purchased from the Jackson Laboratory (Bar Harbor, Me.). At 5 weeks of age, the first cohort of littermate male mice were randomly assigned to either saline intranasal administration (Saline, n=7) or MSC-exo intranasal administration (MSC-exo, n=7). At 5 weeks of age, the first cohort of littermate female mice were randomly assigned to saline intranasal administration (Saline, n=9) or MSC-exo intranasal administration (MSC-exo, n=6).

C57bl/6 mice were bred from adult pairs originally purchased from The Jackson Laboratory (Bar Harbor, Me.). At 5 weeks of age, the first cohort of littermate male mice were given saline by intranasal administration (Saline, n=7) At 5 weeks of age, the first cohort of littermate female mice were randomly assigned to saline intranasal administration (Saline, n=7) and no saline (None, n=11).

Mice were housed in groups of 3-5 littermates per cage. Mice were initially tested for baseline behaviors at 5-7 weeks prior to administration of exosomes, which occurred at 7-9 weeks. (5 ul of exosomes or saline was administered every other day for 14 days, for a total of 35 ul).

Three weeks after exosomes were administered, 6 BTBR-MSC-exo virgin females were placed with one BTBR-saline pregnant female for maternal learning behaviors. Five BTBR-saline virgin females were placed with one C57-saline pregnant female for maternal learning behaviors.

Behavioral Tests:

Open Field:

Mice were placed in a 45×45×45 cm for a total of 20 minutes. Ethovision v10.11 was used to measure total distance moved and the amount of time spent in the center.

Ultrasonic Vocalizations:

Male to female ultrasonic vocalization were tested using Avisoft-RECORDER v. 4.2.21 recording program. The settings included a sampling rate of 250 kHz and a format of 16 bit. For spectrogram generation, recordings were transferred to Avisoft-SASLab Pro Version 5.2.07 and a fast Fourier transformation (FFT) was conducted. Spectrograms were generated with an FFT-length of 256 points and a time window overlap of 50% (100% Frame, FlatTop window). Both BTBR T1tf/J and C57bl/6 males met C57bl/6 females. Each male was placed in separate cage for 1 hour, then a female was placed in the cage. Ultrasonic vocalizations were recorded for the first five minutes of encounter and filmed for male-female social interaction analysis.

Reciprocal Dyadic Social Interaction Test:

The reciprocal dyadic social interaction test (Silverman et al., 2012) was conducted using a 5 week old male C57BL/6 stranger mouse as the social stimulus. The stranger mouse was placed in a 40×40×20 cm cage with the test mouse. Both mice were recorded for 20 minutes; the last 10 min were quantified by an observer blind to treatment. Both mice were isolated for 1 hour prior to the test. Cowlog V3 software was used to score the social contact initiated by the test mouse (Helsinki University, Helsinki, Finland). Scoring was determined by the duration of mice engaging the stranger mouse in social behaviors. The following social behaviours were quantified: nose to nose sniffing (i.e. approach to the front of the stranger), nose to genital sniffing (i.e. approach to the back of the stranger), attacking (i.e. test mouse initiates a fight with the stranger mouse), and avoiding (i.e. when test mouse deliberately avoids interaction when the stranger mouse initiates it). During social interactions, the time spent in repetitive behaviors, namely grooming and digging, were also observed and quantified.

Repetitive Behaviors not During Social Interaction:

Mice were placed alone in an arena with dimensions 40×40×20 cm for 20 min; the last 10 minutes were quantified for grooming and digging. While observing the grooming behavior, the mice were placed in a clean cage not containing wood-chips to prevent digging. While observing the digging behavior, self-grooming was not measured.

Maternal Behavior Learning:

Four c57bl mothers and 3 BTBR mothers were tested for their latency to collect pups and bring them back to the nest. Each mother was tested with 3 pups. If the mother did not bring back the pup to the nest 180 seconds after they were placed outside the nest, it was considered a failure. Each of the mothers shared a cage with three virgin females (learning virgins) for couple of days. BTBR saline and C57 saline virgins spent time with C57bl mother and her pups, and BTBR MSC-exo females spent with BTBR female and her pups. A group of naïve virgins, which was never exposed to pups before was also tested (BTBR naïve virgin, c57bl naïve virgin) During the test, all females were taken out of the cage, and at the end of each test, the mice were returned to their home cage and given 15 minutes of re-acclimation. Each pup was between 2 and 4 days old at the time of testing. Test were filmed with SAMSUNG limp camera.

Water T-Maze Assay:

The water T-maze (Guariglia & Chadman, 2013; Karvat & Kimchi, 2013) was a T-shaped Plexiglass chamber, with three arms of size 22×3×11 cm and a center zone sized 11×3×11 cm. The maze was filled with water 15 cm deep, kept at 25±1° C. A platform with side length 3 cm was submerged so that the top was 0.5 cm below the water level. Each animal had 10 trials each day of the three experiment days, for a total of 30 trials. The animals were put in the starting arm facing the center zone and were given 90 seconds to find the platform. When the animal mounted the platform, it was allowed to stay on it for 5 seconds. If a mouse did not find the platform within 90 seconds, it was gently guided to the platform and allowed to stay on it for 15 seconds. Inter-trial interval was >5 min. On the first and second days, the platform was located in the right arm, while on the third day it was located in the opposite, left, arm; the starting arm was identical each day. A mouse was not permitted to begin the reversal trials until they had succeeded in 8/10 trials, resulting in some mice having an extra day of learning and up to a total of 40 trials. The amount of time taken to reach the platform, the number of errors and the tendency to turn the correct or incorrect way were measured from the time the mouse entered the water until it stood on the platform.

Results

Figure 1:
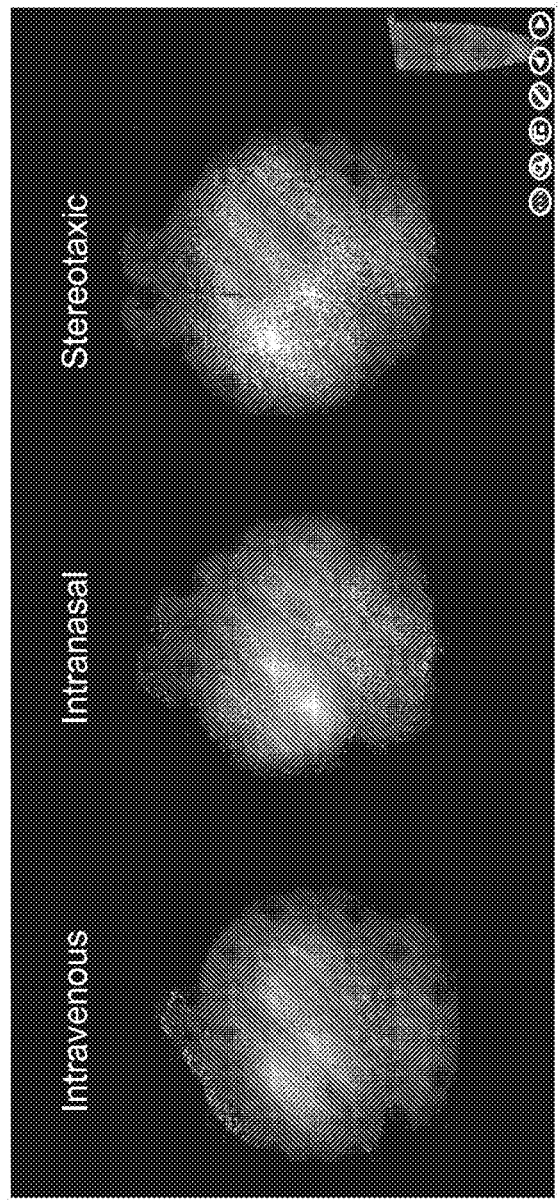
FIG. 1. MSC-exosomes stained with PKH26 when given intravenously, intranasally and stereotactically. The brains were analyzed 1 hour post administration. Stereotactic administration yielded 100%, intranasal, 68.5% and intravenous, 11.2%.

High Efficiency of Intranasal Administration of MSC-Exosomes:

Comparisons between intravenous, intranasal and stereotaxic administration of PKH26 stained exosomes were made. A corrected total cell florescence (CTCF) calculation was used to estimate the efficiency of the different administration strategies (McCloy et al., 2014). Florescence quantification relative to stereotaxic injection showed that 68.5% of intranasal administrated exosomes were found in the brain while 11.2% of intravenous exosomes were found (FIG. 1). Immunostainings DAPI and NeuN showed that the exosomes were found in the cells and on their membranes (FIGS. 2A-B).

MSC-Exosomes Improved Male to Female Ultrasonic Vocalizations:

Ultrasonic vocalizations are considered to be a mating communication form between male and female mice. Communication deficits is a core symptom in autism, therefore, the effect of the treatment on this type of behavior was assessed. BTBR saline mice emitted 317 syllables in the first 5 minutes of interaction with female (SEM=39.4) while BTBR MSC-exo emitted 571 syllables during the same time, which is an increase of 180% (SEM=74) whilst C57bl mice (control) emitted 854.5 syllables per first 5 minutes (SEM=65.2). (FIG. 3A, ANOVA1, F=19.2 P<0.001). There was no significant difference in time spent sniffing the female's genitalia or face, meaning the effect seemed to specifically impact the ultrasonic vocalizations and not the interest in the female's pheromones (FIG. 3B). Qualitatively it can be seen from the spectrograms that BTBR MSC-exo vocalizations became more complex and long compared to the BTBR saline group, making them more similar to C57bl (FIG. 3C).

MSC-Exosomes Improves Male to Male Social Interaction and Repetitive Behaviors During Social Interaction:

Mice were tested for male to male interaction before and after MSC-exo or saline administration. Intra-subject analysis shows BTBR MSC-exo group was significantly improved after treatment and spent longer time in social contact with stranger males, while BTBR saline and C57bl saline groups were not impacted (FIG. 4A, paired t-test. t<0.0001). Groups' comparison analysis shows that before treatment there is no difference between BTBR MSC-exo and BTBR saline basal behaviors, and both of them significantly differ from c57bl saline basal behavior (ANOVA1, F=14.4, p<0.01). After treatment, BTBR MSC-exo is significantly different from the BTBR saline group (ANOVA1, F=9.44, p<0.01).

Repetitive behaviors were also measured during social interaction. Intra-subject analysis shows BTBR MSC-exo group was significantly improved after treatment and spent less time in repetitive behaviors, while BTBR saline and C57bl saline groups were not affected (FIG. 4B, paired t-test. t<0.001). Groups' comparison analysis shows that before treatment there is no difference between BTBR MSC-exo and BTBR saline basal behaviors, and both of them significantly differ from c57bl saline basal behavior (ANOVA1, F=13.71, p<0.001). After treatment, BTBR MSC-exo is not significantly different from the BTBR saline group and C57bl group, however there is a significant change from the BTBR MSC-exo before and after treatment.

MSC-Exosomes Decreases Self-Grooming and Digging:

Self-grooming and digging was also measured without social interactions. Mice were tested for male to male interaction before and after MSC-exo or saline administration. In grooming test intra-subject analysis showed BTBR MSC-exo group was significantly improved after treatment and spent less time self grooming, while BTBR saline and C57bl saline groups were not changed (FIG. 4A, paired t-test. t<0.05). Groups' comparison analysis shows that before treatment there is no difference between BTBR MSC-exo and BTBR saline basal behaviors, and both of them significantly differ from c57bl saline basal behavior (ANOVA1, F=12.4, p<0.05). After treatment, BTBR MSC-exo is significantly different from the BTBR saline group (ANOVA1, F=13.83, p<0.01).

MSC-Exosomes Improves Cognitive Rigidity in Water T-Maze:

The Water T-maze Assay was used to analyze learning behaviors and cognitive rigidity. Due to different swimming capacities between c57bl and BTBR mice, their behavior in the test was not comparable, and therefore c57bl mice were excluded. Altogether, BTBR MSC-exo treated mice made significantly less mistakes in reversal learning in all 10 trials (FIG. 6A). Analyzing success rate on each trial of reversal conditions shows that from trial 4 MSC-exo treated mice had higher success rates than the saline group at turning correctly (FIG. 6B).

MSC-exo improves maternal behavior learning: All C57bl mothers collected back all the pups (12/12) to the nest in an average time of 9.9 sec (SEM=1.08). None of C57bl naïve virgins collected any of the pups back within 180 seconds. The C57bl learning virgins group collected back all the pups at average time of 38.3 sec (SEM=11.9). Just one of three tested BTBR mothers collected the pups, however after 150 sec she did had not brought them back to the nest, but rather placed them in random places; her behavior was disorganized compared to C57bl mothers and learning virgins. None of the BTBR naïve virgins collected any of the pups within 180 seconds. None of BTBR learning virgins collected any of the pups, even after spending days with a C57bl mother. BTBR MSC-EXO collected all pups at average time of 55.7 seconds (SEM=12.8), interestingly, BTBR MSC-exo spent days with a BTBR mother who was incapable of retrieving pups herself.

Example 2

MSC-Derived Exosomes for Treating Schizophrenia

Materials and Methods

Sensitivity to Amphetamine-Induced Hyperlocomotor Activity:

The experiment took place in several phases. In the first phase, 30 C54/bl mice were randomly allocated to 3 groups; a saline treated group, a PCP-treated group and a PCP+ exosome-treated group (the treatment group). The PCP groups received daily subcutaneous injections of 10 mg/kg of PCP for a 14 day period. At the same time, the saline group received an equivalent volume of saline injections and the exosomes group received PCP injections as well as 2 μl of exosomes by intranasal administration. The other groups received 2 μl of saline using the same technique. A week after the end of injections the mice underwent behavioral tests.

All groups were subjected to systemic amphetamine injection and monitored in the open field test for 120 minutes and measured for activity index, averaged every 5 minutes.

Latent Inhibition.

The effect of exosomes on central information processing in PCP-treated mice were analyzed by assessing the acoustic startle reflex. Three mice from each groups were assigned to the non-pre-exposed (NPE) group and seven mice were allocated to the pre-exposure (PE) group. PE mice were presented with 50 presentations of a 30-s tone stimulus (the conditioned stimulus—CS) while non-pre-exposed (NPE) subjects were confined to the chamber for an equivalent period of time without any stimulus presentation. Immediately afterwards, both PE and NPE groups underwent conditioning, comprised of three pairing between CS and an unconditioned stimulus (US): A tone stimulus followed immediately by the delivery of a 1-s foot-shock set at 0.3 mA. After 24 hours the test phase was conducted. Following an initial period of 360 s acclimatization, the tone CS was delivered and was continued for 90 s, in which the time of conditioned freezing to the tone stimulus was evaluated.

Social Interaction in 3-Chamber Social Interaction:

3 groups of mice were treated as follows:
1. saline group (n=19),
2. PCP group (n=17),
3. PCP+exosomes (n=18)

Results

Sensitivity to Amphetamine-Induced Hyperlocomotor Activity:

Following amphetamine injection, the locomotor activity of all amphetamine-treated mice increased and peaked at about 40 min post-injection. Throughout the entire measuring period the enhancing effect of systemic amphetamine was significantly more pronounced in the PCP-treated subjects.

As illustrated in FIGS. 8A-B and 10, the PCP-treated mice (with no exosome treatment) were more active and moved a greater distance than the saline-treated negative control group and also were more active than the exosome-treated group. This is most apparent after 40 min, after the peak of activity inspired by the amphetamine.

Latent Inhibition:

No difference was found between subjects during the test phase (results not shown). During conditioning, both saline-treated groups and exosome-treated group displayed a significant difference between their freezing response in the PE and NPE groups, while PCP treated group did not show a significant increase in freezing of NPE (FIG. 9), indicating a reduced LI effect in PCP-treated mice and a positive effect of the exosome treatment.

Sensitivity to Amphetamine-Induced Hyperlocomotor Activity:

Locomotor activity of all amphetamine-treated mice increased and peaked at about 40 min post-injection. Throughout most of the measuring period the enhancing effect of systemic amphetamine was significantly more pronounced in the PCP-treated subjects. As illustrated in FIG. 10, the saline-treated group (group 4) which received intranasal administration of exosomes were not affected (there was no significant difference from the saline group (1). PCP-treated mice (group 2) were more active and moved a greater distance than the saline-treated control group (group 1) and also more active than the exosome-treated group (group 3). This is most apparent after 40 min, after the peak of activity inspired by the amphetamine.

Social Interaction in 3-Chamber Social Interaction:

In the 3-chamber paradigm the PCP-treated mice (n=17) showed an increased preference for the empty-cage (i.e. non-social stimulus) over the stranger-habituated cage (social stimulus), as revealed by the preference index. The saline treated group (n=19) exhibited a preference for the mouse-habituated cage while the exosome-treated mice (n=18) showed the highest preference for the social stimulus (FIG. 11).

Example 3

Comparison of Exosomes from Bone Marrow Derived MSC Vs. Neuronal Stem Cells in BTBR Model of Autism Materials and Methods NSC Derived Exosomes:

The neural stem cell line (CTX0E03) (ReNeuron) was used.

Treatment Groups:

Mice received intranasal administration of MSC-exo (N=5), NSC-exo (N=5) or Saline (N=7) for 12 days, 5 µL a day (2.5 µL×2), every other day (total of 30 µL per mouse).

Results

Figure 12A:
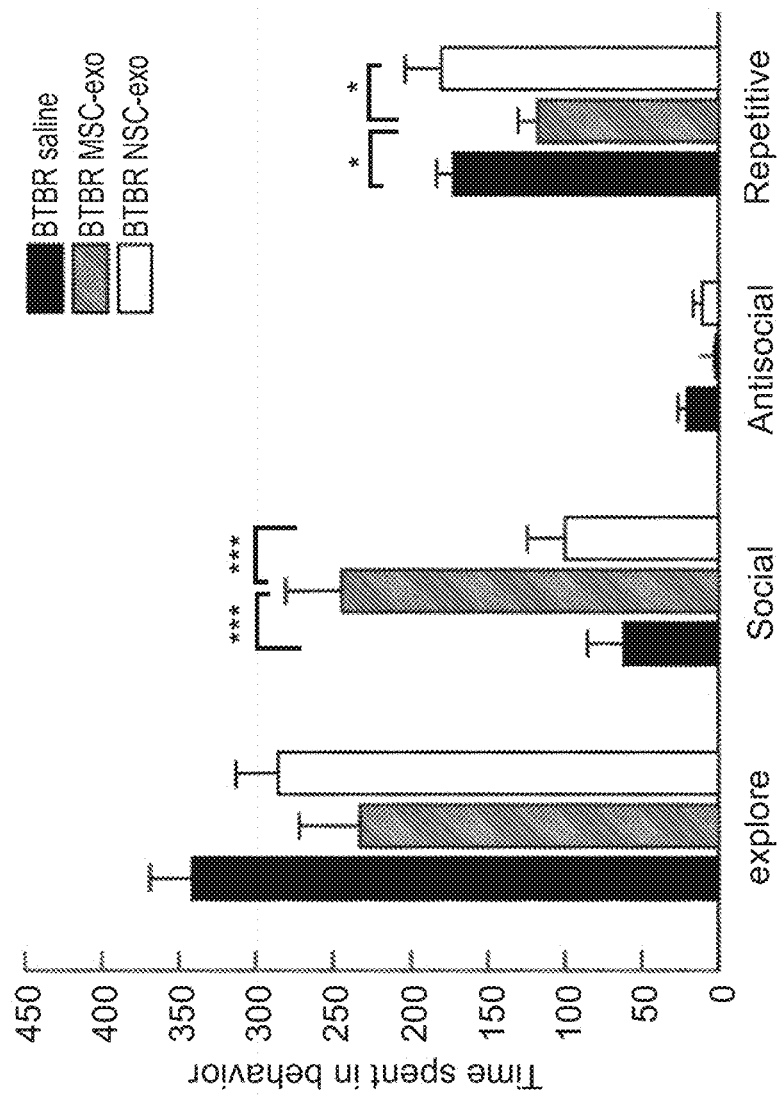
FIG. 12A is a graph illustrating that MSC derived exosomes but not NSC derived exosomes improve male to male social interaction and reduce repetitive behaviors during social interaction in BTBR mice. Only MSC-exo treated mice presented significant increase in time spent in social interaction and significant reduction in repetitive behaviors compared to saline treated and NSC-exo treated mice (unpaired T-test, *$p<0.05$, ***$p<0.001$). Data is presented as mean+SEM.

As illustrated in FIGS. 12A-B, administration of MSC-derived exosomes increased social interaction, reduction in repetitive behaviors and increased communication compared to the saline treated group, whilst neuronal stem cell-derived exosomes (NSC-exo) treated mice did not present the same behavioral difference compared to saline treated group (ANOVA1, $F_{2,14}=4.28$, $p<0.05$, Bonfferoni).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating an autism spectrum disorder (ASD) in a subject comprising administering to the subject a therapeutically effective amount of microparticles derived from mesenchymal stem cells, thereby treating the autism spectrum disorder.

2. A method of treating a neurodevelopmental disorder in a subject, comprising administering to the subject a therapeutically effective amount of particles derived from mesenchymal stem cells (MSCs), thereby treating the neurodevelopmental disorder in the subject, wherein the neurodevelopmental disorder is attention deficit hyperactivity disorder.

3. A method of treating a neurodevelopmental disorder in a subject, comprising administering to the subject a therapeutically effective amount of particles derived from mesenchymal stem cells (MSCs), thereby treating the neurodevelopmental disorder in the subject, wherein the neurodevelopmental disorder is obsessive compulsive disorder.

4. The method of claim 2, wherein said administering comprises intranasally administering.

5. The method of claim 2, wherein said particles are selected from the group consisting of exosomes, microvesicles, membrane particles, membrane vesicles, ectosomes and exovesicles.

6. The method of claim 5, wherein said particles are exosomes.

7. The method of claim 2, wherein said mesenchymal stem cells are derived from dental pulp, bone marrow or adipose tissue.

8. The method of claim 2, wherein said MSCs are human MSCs.

9. The method of claim 3, wherein said administering comprises intranasally administering.

10. The method of claim 3, wherein said particles are selected from the group consisting of exosomes, microvesicles, membrane particles, membrane vesicles, ectosomes and exovesicles.

11. The method of claim 10, wherein said particles are exosomes.

12. The method of claim 3, wherein said mesenchymal stem cells are derived from dental pulp, bone marrow or adipose tissue.

13. The method of claim 3, wherein said MSCs are human MSCs.

14. The method of claim 1, wherein said administering comprises intranasally administering.

15. The method of claim 1, wherein said particles are exosomes.

16. The method of claim 1, wherein said mesenchymal stem cells are derived from dental pulp, bone marrow or adipose tissue.

17. The method of claim 1, wherein said MSCs are human MSCs.

* * * * *